United States Patent [19]

Tanaka et al.

[11] Patent Number: 5,865,799
[45] Date of Patent: Feb. 2, 1999

[54] PREFILLED SYRINGE

[75] Inventors: Nobuo Tanaka, Mishima-gun; Jotaro Kishimoto, Nishinomiya; Kotaro Wakamatsu, Ikeda; Takayuki Hagihara, Suita; Seiji Ohtani, Ibaragi, all of Japan

[73] Assignee: Takeda Chemical Industries

[21] Appl. No.: 899,053

[22] Filed: Jul. 23, 1997

Related U.S. Application Data

[62] Division of Ser. No. 530,674, Sep. 19, 1995, Pat. No. 5,716,339, which is a division of Ser. No. 52,622, Apr. 27, 1993, abandoned.

[30] Foreign Application Priority Data

| Apr. 30, 1992 | [JP] | Japan | 4-028792 U |
| Apr. 30, 1992 | [JP] | Japan | 4-028793 U |
| Sep. 18, 1992 | [JP] | Japan | 4-065171 U |
| Sep. 21, 1992 | [JP] | Japan | 4-065612 U |

[51] Int. Cl.$^6$ .................................................. A61M 37/00
[52] U.S. Cl. ............................................... 604/89; 604/86
[58] Field of Search ................................. 604/82, 83, 85, 604/86, 89, 91, 92, 191, 232, 234, 411–416

[56] References Cited

U.S. PATENT DOCUMENTS

| Re. 34,845 | 1/1995 | Vetter et al. . |
| 1,961,023 | 5/1934 | West . |
| 2,688,967 | 9/1954 | Huber . |
| 3,330,282 | 7/1967 | Visser et al. . |
| 3,807,119 | 4/1974 | Shields . |
| 3,967,759 | 7/1976 | Baldwin et al. . |
| 4,067,333 | 1/1978 | Reinhardt et al. . |
| 4,235,235 | 11/1980 | Bekkering . |
| 4,424,057 | 1/1984 | House . |
| 4,439,184 | 3/1984 | Wheeler . |
| 4,496,344 | 1/1985 | Kamstra . |
| 4,599,082 | 7/1986 | Grimard . |
| 4,613,326 | 9/1986 | Szwarc . |
| 4,668,223 | 5/1987 | Grotenhuis . |
| 4,792,329 | 12/1988 | Schreuder . |
| 4,820,286 | 4/1989 | van der Wal . |
| 4,822,340 | 4/1989 | Kamstra . |
| 4,874,381 | 10/1989 | Vetter . |
| 4,968,299 | 11/1990 | Ahlstrand et al. . |
| 5,069,670 | 12/1991 | Vetter et al. . |
| 5,080,649 | 1/1992 | Vetter . |
| 5,139,490 | 8/1992 | Vetter et al. .................. 604/232 X |
| 5,364,369 | 11/1994 | Reynolds . |
| 5,383,864 | 1/1995 | Van der Heuvel . |
| 5,665,068 | 9/1997 | Takamura ................................. 604/90 |

FOREIGN PATENT DOCUMENTS

| 0 311 324 | 10/1988 | European Pat. Off. . |
| 0 360 313 A1 | 8/1989 | European Pat. Off. . |
| 0 520 618 A2 | 5/1991 | European Pat. Off. . |
| 75 06745 | 3/1975 | France . |
| 1 616 199 | 5/1972 | Germany . |
| 2258373 | 6/1973 | Germany . |
| 3924830 | 7/1989 | Germany . |
| 705392 | 3/1954 | United Kingdom . |

Primary Examiner—Ronald Stright, Jr.
Assistant Examiner—A. T. Nguyen
Attorney, Agent, or Firm—Wenderoth, Lind & Ponack, L.L.P.

[57] ABSTRACT

A prefilled syringe capable of separate storage of different substances before use. It includes a tubular body having an injection needle at one end and a plunger at the other end, and a partition axially slidable in the tubular body. The partition includes a front part and a rear part independent of each other, and as a whole divides the interior space of the tubular body into a front compartment and a rear compartment in a sealing manner for storing mutually different substances. A bypass is disposed generally between the front and rear compartments to introduce the substance in the rear compartment into the front compartment when the partition is slid under pressure provided by the plunger to be adjacent to the bypass to thereby mix the substances immediately prior to injection.

6 Claims, 8 Drawing Sheets

Fig. 6A  Fig. 6B
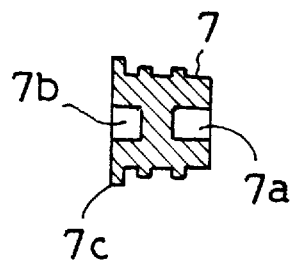 
Fig. 7A  Fig. 7B
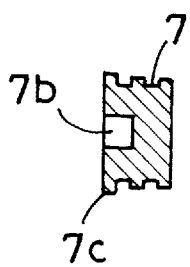 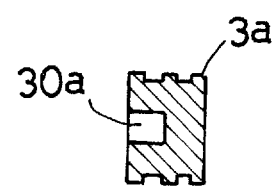
Fig. 8A  Fig. 8B
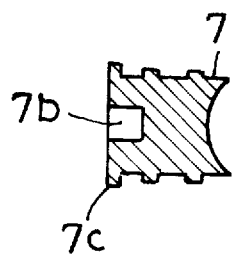 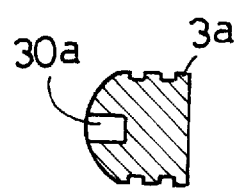
Fig. 9A  Fig. 9B
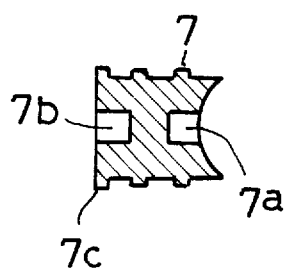 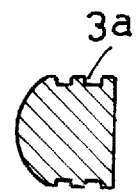

PREFILLED SYRINGE

This is a Rule 60 Divisional application of Ser. No. 08/530,674, filed Sep. 19, 1995, now U.S. Pat. No 5,716,339, which is a Divisional of Ser. No. 08/052,622, filed Apr. 27,1993, now abandoned.

FIELD OF THE INVENTION

The present invention relates generally to a prefilled syringe, and more particularly to a prefilled syringe capable of separate storage of at least two different substances before use, wherein one of the substances is, for example, a medicinal component, and the other is, for example, a vehicle, such as a dissolving agent or a dispersing agent, as the case may be. In this specification the term "prefilled" or "filled" relates to a syringe in which a medicament is stored until use. This is in contrast to storing the medicament separately from the syringe in a vial and then drawing it from the vial with the syringe immediately prior to use.

BACKGROUND OF THE INVENTION

In order to explain the background of the invention, a prefilled syringe of a known type will be described with reference to FIGS. 15 to 19.

The conventional prefilled syringe includes a tubular body 31 and a plunger 32 with a rod. The tubular body 31 has a front compartment 34 and a rear compartment 35 separated by a partition 33 which is movable axially with the tubular body 31. The front compartment 34 includes a bypass 36 produced in the form of a recess. So long as the partition 33 stays in the rear compartment 35, it separates the two compartments 34 and 35 from each other in a sealing manner as shown in FIG. 15, but when it is moved into the front compartment 34, an opening is formed between the partition 33 and the bypass 36 in the front compartment 34. The movement of the partition 33 is performed by pushing the plunger 32. When the partition 33 is moved into the front compartment 34, the liquid contained in the rear compartment 35 is introduced into the front compartment 34 through the bypass 36 and dissolves or disperses the medicinal component in the front compartment 34 or becomes mixed therewith, as the case may be. In this way an injection liquid is obtained in the front compartment 34, and is ready to be ejected from the tubular body 31. This exemplary prefilled syringe is disclosed in Japanese Patent Publication (allowed) No. 49-14465.

FIG. 19 shows a modified version in which the partition 33 is provided with ring-shaped ribs 33a so as to enable the partition 33 to smoothly slide on and along the inside wall of the tubular body 31 with minimum contact therewith. The conventional prefilled syringes have the following problems.

The front compartment 34 is filled with a powdery medicinal component. When the medicinal component is liquid, it is first filled in the front compartment 34 and then freeze-dried into a powdery state as shown in FIG. 17. A vehicle L for dissolving or dispersing the medicinal component P is placed in the rear compartment 35. In this way a finished syringe is obtained. If the vehicle L is to be sterilized by steam, the syringe is closed by a cap 37 as shown in FIG. 17. However, this steam sterilization is likely to denature the medicinal component P in the front compartment 34. As a solution to this problem, an alternative method is that, after the vehicle L is sterilized by steam, the medicinal powder P is placed in the front compartment 34. However, this method is disadvantageous in that droplets of water or moisture from the steam are likely to stay on or impregnate or penetrate and later escape from the partition 33 (commonly made of rubber), thereby detrimentally wetting the desiccated powdery medicinal component P.

Since a powdery medicinal component tends to become unstable in the presence of water, it is essential to dry out at least the side of the partition 33 facing the front compartment 34 which contains a desiccated powdery injection, component. It is common practice to dry the syringe at a temperature of 100° C. or more for hours, but this high temperature unfavorably affects the vehicle L in the rear compartment 35. As a result, this high temperature heat-drying method cannot be adopted.

It is common practice to provide the partition 33 with annular or ring-shaped ribs 33a along the periphery so as to reduce friction between the parition 33 and the inside wall of the body 33. In this case, they unavoidably form one or more ring-shaped grooves (G) therebetween. These grooves (G) trap the injection liquid when the injection liquid is ejected from the rear compartment 35 to the front compartment 34 so that the injection liquid remains unused in the grooves (G). Specifically, the injection liquid is pushed axially through the bypass 36, but the ribs 33a catch some of the liquid through the bypass 36 and divert it circumferentially into the grooves (G) where it is trapped and remains unused. This results in waste of the injection liquid.

In using a prefilled syringe, it is important to mix the medicinal component and the vehicle into a homogeneous injection liquid. Normally, immediately prior to use, the syringe is swung by hand to mix these substances. However, difficulty arises in pushing the plunger to the appropriate position; if the plunger is pushed excessively into the tubular body, it is likely that the medicinal component and vehicle are injected through the syringe without being sufficiently mixed. If the plunger stays in the midst of the bypass 36, backflow of the liquid is likely to occur from the front compartment to the rear compartment. If the insertion of the plunger is short of the appropriate distance, the vehicle L in the rear compartment fails to enter the front compartment through the bypass.

In order to solve this problem, applicants have considered indicia or markings at an appropriate position on the plunger where the plunger is to be stopped. This marking method encounters the difficulty of restraining the plunger from axial movement relative to the tubular body while the mixing is effected by swinging the syringe. Besides, attention must be constantly paid to the marking while the rod is pushed. The conventional prefilled syringe has no device which has solved this problem.

SUMMARY OF THE INVENTION

A prefilled syringe according to the present invention includes a tubular body having a front end closable by a plug and adapted to accept an injection needle and a rear end closable by a plunger with a rod. A movable partition divides the interior space of the tubular body into a front compartment and a rear compartment in a sealing manner, the partition including a front part and a second part which are independent of each other. The front compartment stores a first substance and the rear compartment stores a second substance, and a bypass is produced in the front compartment, with the partition being axially shorter than the bypass, so as to introduce the second substance into the front compartment therethrough when the partition is moved into the front compartment under pressure provided by the plunger. Thereby a predetermined action is effected such as dispersing or dissolving, between the first and second substances in the front compartment.

According to another aspect of the present invention, the prefilled syringe includes a tubular body having a front end closable by a plug and adapted to accept an injection needle and a rear end closable by a plunger with a rod which is movable in the tubular body. A movable partition divides the interior space of the tubular body into a front compartment and a rear compartment in a sealing manner, the front compartment storing a first substance and the rear compartment storing a second substance. The partition includes circumferentially extending ring-shaped first ribs along the periphery thereof, with a ring-shaped groove interposed therebetween, and second transverse ribs for bridging and subdividing the groove into small recesses. The second ribs having the same height as of the ring-shaped first ribs. A bypass is also produced in the front compartment so as to introduce the second substance into the front compartment therethrough when the partition is moved into the front compartment under pressure provided by the plunger, thereby effecting a predetermined action, such as dispersing or dissolving between the first and second substances in the front compartment.

The syringe and rod may be provided with a respectively engaging means for enabling the plunger to stop at an appropriate position so that the predetermined action such as dispersing or dissolving is carried out with the two substances being fully confined in the front compartment.

Thus, the invention described herein has the advantages of (1) providing a prefilled syringe which protects the first substance in the front compartment against a pre-treatment such as steam sterilization applied to the second substance stored in the rear compartment, (2) which prevents the injection liquid from staying behind and remaining unused in the syringe, and (3) which provides optimum conditions for swinging the syringe for stirring the substances in the front compartment.

These and other advantages of the present invention will become apparent to those skilled in the art upon reading and understanding the following detailed description with reference to the accompanying figures.

BRIEF DESCRIPTION OF THE DRAWINGS

This invention may be better understood, and its numerous objects and advantages will become apparent to those skilled in the art, by reference to the accompanying drawings.

FIGS. 2(A) and 2(B) show a process of assembling the syringe, wherein FIG. 2(A) shows a first step at which a vehicle is put in one compartment and FIG. 2(B) shows a second step at which a medicinal component is put in the other compartment;

FIGS. 6 to 9 show various types of plugs and the front part of a partition used in combination with a respective plug;

DETAILED DESCRIPTION OF THE PREFERRED EMBODIMENT

EXAMPLE 1

Figure 1:
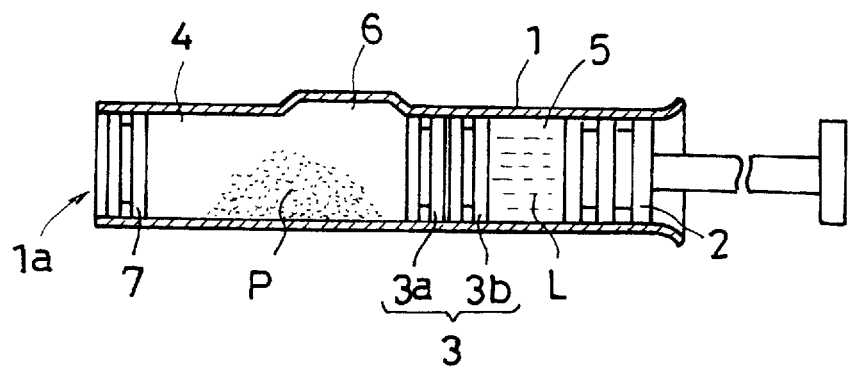
FIG. 1 is a schematic cross-sectional view through an embodiment of a syringe of the present invention.

Referring to FIG. 1, the exemplary prefilled syringe has a generally tubular body 1 which is open at the front and rear ends, and a plunger 2 having a push rod slidably inserted into the body 1 through the rear end. The push rod may be detachable. The body 1 includes a front compartment 4 and a rear compartment 5 separated by a partition or sealing means 3 in a liquid-tight manner, the partition 3 being slidable axially in the body 1 under pressure provided by the plunger 2. The front compartment stores a medicinal component P as a powder, microcapsules, granules, tablets, and liquids, or any other form or state, and the rear compartment 5 stores a vehicle L in a liquid or any other form for dissolving or dispersing the medicinal component P, or for becoming mixed therewith. The body 1 is provided with a bypass 6 on the inside wall thereof. The bypass or bypass means 6 is produced in the form of a recess for introducing the vehicle L in the rear compartment 5 into the front compartment 4, which will be described in detail.

The partition 3 includes a front part or portion or bypass stopper or stopper plug 3a and a rear part or portion or bypass stopper or stopper plug 3b which are independent of each other and separately movable. Each of the partition parts or stoppers 3a, 3b extends radially and the inner walls of the body 1 to seal the rear compartment 5 from the front compartment 4 independently of the other partition part with which it is paired. The combined axial length of the partition parts 3a, 3b is less than the axial length of the bypass 6 and permit the injection liquid to be conveyed from the rear compartment 5 to the front compartment 4. When the partition 3 is between the bypass 6 and the rear end of the syringe, the partition parts preferably engage each other, but if they are slightly spaced because of air being compressed therebetween when the they are front part 3a is slid into the body during assembly, the axial distance of such a space is less than the axial width of one of the partition parts 3a and 3b. In use, as the plunger 2 is initially pushed, the air between the partition parts 3a and 3b is compressed by the movement of the rear part 3b. This compression urges the front part 3a forward until the rear face of the front partition part 3a reaches the bypass 6, whereupon any air between the partition parts 3a and 3b escapes therefrom to the bypass 6 to permit the partition parts 3a and 3b to engage each other if not already engaged. It is in this engaged state in which the partition 3 travels the remainder of the syringe.

The front end portion 1a of the body 1 is closed by a movable plug 7. As described below in detail, the front end 1a of the syringe is capped with a cap carrying an injection needle. Herein, the front, end portion of the syringe, covers the front end of the syringe and a further portion extending slightly toward the bypass 6 from the front end of the syringe. Hereinafter, the front end portion of the syringe may be referred to as the "front end of the syringe". It should be noted that the plug 7, before actuation of the plunger, may be spaced from the extreme front end of the syringe to minimize the chances that the plug 7 will prematurely slide out of the front end. The distance that the plug 7 is spaced from the extreme front end may depend upon the volume of the substances to be mixed. Such a volume may define the space between the bypass 6 and the plug 7, and hence the distance between the plug 7 and the extreme front end.

Figure 4:
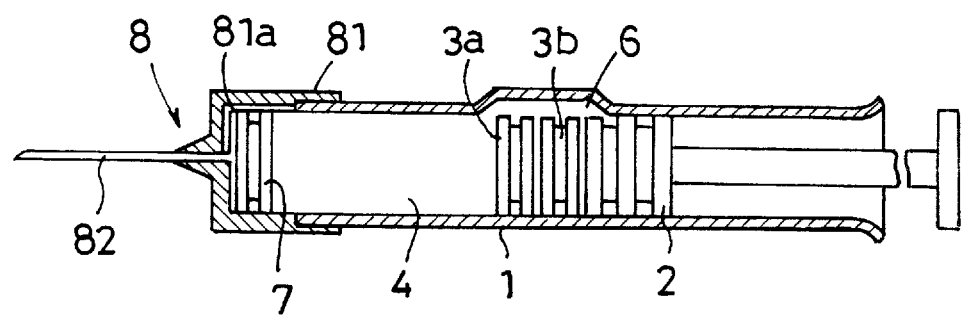
FIG. 4 is a cross-section through the syringe of FIG. 3, shown in use.

As stated above, the bypass 6 has a length longer than the total thickness of the front part 3a and the rear part 3b as shown in FIG. 4. Furthermore, the combined axial length of the partition parts 3a and 3b, and the plunger 2 (exclusive of the push rod) is greater than the axial length of the bypass 6 to prevent backflow of air or liquid from the front compartment 4 to the rear compartment 5.

The plunger 2 is pushed to the left (FIG. 1) whereby the front part 3a and rear part 3b of the partition 3 are moved together in a spaced apart fashion under pressure provided by the plunger 2. When the parts 3a and 3b reach the bypass 6 as shown in FIG. 4, the vehicle L in the rear compartment 5 is introduced into the front compartment 4 through the bypass 6, thereby effecting a desired action such as dispersing, dissolving or mixing between the medicinal component P and the vehicle L. In this way an injecting medicine (or simply an injection) is obtained in the front compartment 4. By further pushing the plunger 2, the injection is ejected through an injection needle 82.

Figure 2A:
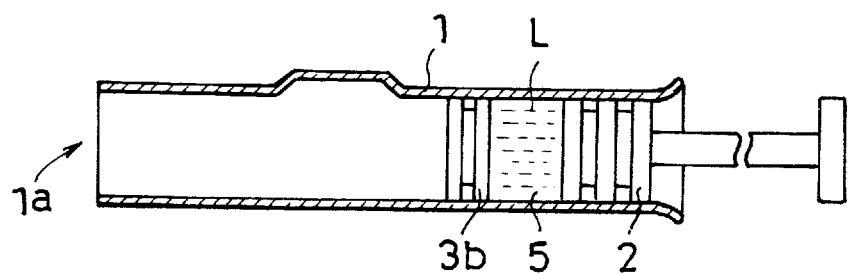
Figure 2B:
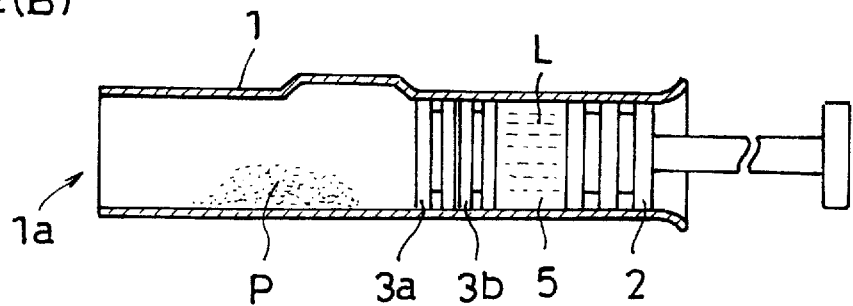

The prefilled syringe is assembled as shown in FIGS. 2A and 2B.

Referring to FIG. 2A, the rear part 3b of the partition 3 is inserted in the body 1, and the vehicle L is put in the rear compartment 5. Then the plunger 2 is inserted. The vehicle L is heat sterilized by dry steam, and then the inside surface of the front compartment 5 is air dried typically with some heat (for example, up to 50°–60° C.) as long as such heat does not damage the substance in the rear compartment 5. During the step of sterilization, the outer ends of the rear stopper 3b and plunger 2 are exposed to the dry steam and may absorb or take in moisture, which may diffuse into the rear stopper 3b or plunger 2. This moisture, over a period of time, may escape by diffusion or some other means out of the end of the rear stopper 3b or plunger 2 into which it entered. This emanating moisture may then adversely affect the hygroscopic powder which is contained in the front compartment 4.

After the front compartment 4 has been dried and as shown in FIG. 2B, the front part 3a of the partition 3, which is kept away from any moisture, is inserted into the body 1 through the front end 1a until it comes relatively near to or into contact with the rear part 3b so as to be adjacent thereto. A dose of powdery medicinal component P is placed in the front compartment 4, and then the front end 1a is closed by the plug 7. In this way a finished syringe is obtained.

When the vehicle L is sterilized by steam, the rear part 3b of the partition 3 becomes wet with deposition of dew or saturated with moisture. While much of this moisture is removed when the front compartment 4 is dried, some of this moisture remains in the rear stopper 3b only to diffuse out over a period of time. The front part 3a is kept dry and away from the sterilization process. The front part 3a thus seals the front compartment 4 against any moisture which may escape from the rear partition part 3b.

Figure 3:
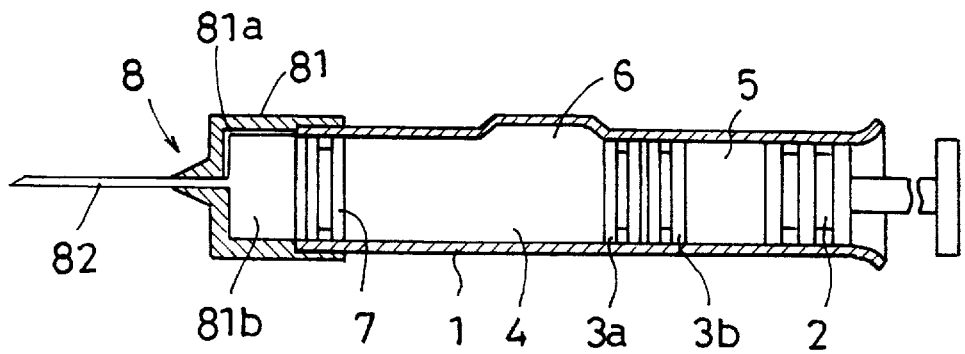
FIG. 3 is a cross-section through the syringe of FIG. 1, provided with a cap into which a plug slides and an injection needle fixed to the cap.

An injection needle 82 can be fixed to the syringe 1 in various manners, as shown in FIGS. 3 and 5–9. A first example is shown in FIG. 3.

The example shown in FIG. 3 has the front end 1a capped with a cap 8 which includes a skirt 81 carrying an injection needle 82. The skirt 81 includes a groove 81a on the inside surface. The groove 81a communicates with the needle 82. The reference numeral 81b denotes a space adapted to receive the plug 7 as shown in FIG. 4.

When the plunger 2 is pushed to the left (FIG. 4), the plug 7 is moved into the space 81b, and the vehicle L in the rear compartment 5 is introduced into the front compartment 4 through the bypass 6. By further pushing the plunger 2, after the syringe is shaken or swung to mix the liquid and drug, the injection is introduced into the needle 82 through the groove 81a. The needle 82 can have been previously fixed to the cap 8, or it can be fixed after the cap 8 has been capped on the syringe 1.

Alternatively, the plug 7 may be arranged, at assembly, to be placed at a distance from the front end of the syringe such that in use, when it is pushed by the plunger 2, it will remain in the front end. This arrangement, and the later mentioned safety engagement means, are cooperatively effective to fully confine the front compartment 4 in a sealing manner.

The examples shown in FIGS. 5 to 9 use a double-pointed needle 10.

Figure 5:
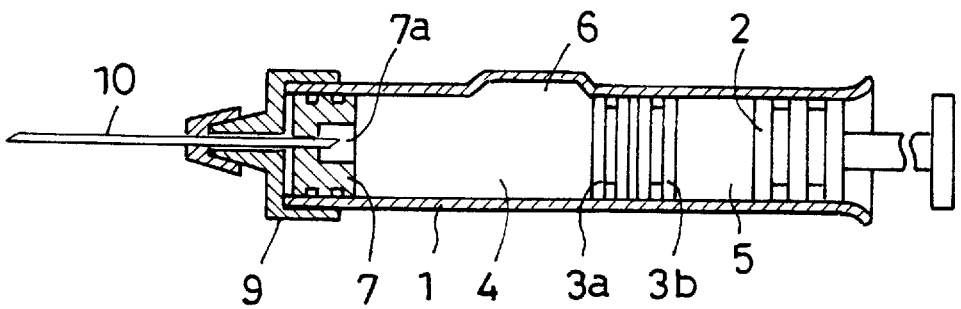
FIG. 5 is a cross-section through the syringe which is provided with a stationary plug and a double-pointed injection needle at a forward open end.

The example shown in FIG. 5 uses a stationary plug 7 and a cap 9 holding a double-pointed needle 10, which projects into the front compartment 4 through the plug 7. This embodiment is advantageous in that it saves the labor of fixing the injection needle 10, and the needle 10 can be readily connected to the front compartment 4 by fixing the cap 9 to the front end 1a. The plug 7 is provided with a recess 7a on the inner side, which allows the injection to gather therein and to be funneled to or collected in the vicinity of the inlet of the needle 10, thereby preventing the injection liquid from staying behind and remaining unused. This avoids waste of the injection liquid.

FIG. 6 shows another example of a plug for a double-pointed needle, wherein the plug 7 has an additional recess 7b on the outer side, the recesses 7a and 7b being aligned with each other, thereby facilitating the passage of the needle 10 because of the reduced thickness of the plug 7. In this example, the respective plug 3A has a flat front face.

FIG. 7 shows another example, characterized in that the face of the front part 3a of the partition 3 is provided with a recess 30a which is aligned with the recess 7b on the outer side of the plug 7 so as to accommodate the needle end projecting through the plug 7. Because of the flat rear face of the plug 7 it is easy to ascertain that the injection needle end is projected into the front compartment 4 through the plug 7.

FIG. 8 shows a further modified plug 7 having a concave surface on the inner side and the front part 3a having a convex surface at its forward end or front face which is complementary with the concave surface of the plug 7 when the partition 3 is pushed by the plunger 2 and brought into contact with the plug 7.

This structure of FIG. 8 is advantageous in that bubbles tend to gather in the center of the concave surface of the plug 7 when the syringe 1 is raised upright prior to injection, thereby facilitating the removal of the bubbles through the injection needle 10.

FIG. 9 shows a modification to the example of FIG. 8, characterized in that the plug 7 is provided with a recess 7a in the concave surface, the recesses 7a and 7b being aligned with each other, with the front part 3a of the partition 3 having no recess. The recess 7a in this modification functions like the recess 7a as described with respect example of FIG. 5.

The examples shown in FIGS. 6 to 9 may have a ring-shaped flange 7c which ensures sealing contact between the plug 7 and the inside wall of the syringe 1. The flange 7c is not necessarily required if the diameter of the plug 7 is precisely calculated such that the plug 7 adequately fits in a sealing manner in the syringe 1. The bypass parts or stoppers 3a, 3b, plug 7, and plunger 2 are preferably formed of an elastomer such as synthetic rubber.

In the exemplary or preferred embodiment, the partition 3 is composed of the front part 3a and the rear part 3b, the latter of which participates in the steam sterilization of the vehicle in the rear compartment 5, and the former of which minimizes or prevents moisture of the rear part 3b from reaching the powdered medicament. However, if desired, the sealing means may include other means for minimizing the emanation of moisture to the hygroscopic powder. Such means may include a thin moisture-impenetrable seal placed directly on the front face of the rear stopper 3b or comprise a rear stopper 3b formed of a material which is impenetrable to moisture.

EXAMPLE 2

Figure 10:
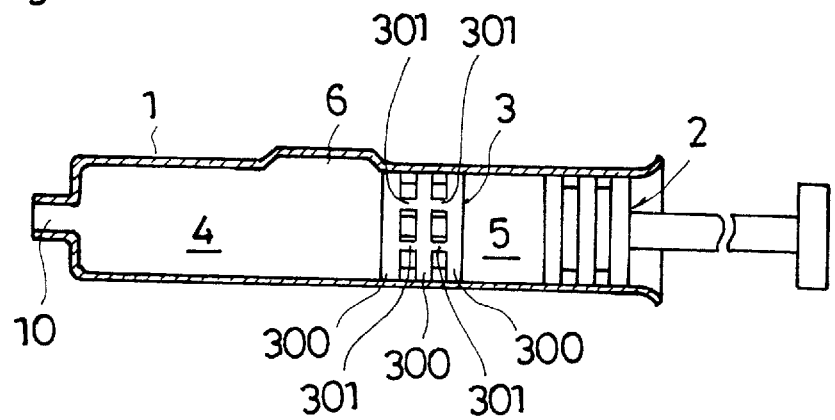
FIG. 10 is a cross-section through a second embodiment of the invention.
Figure 11:
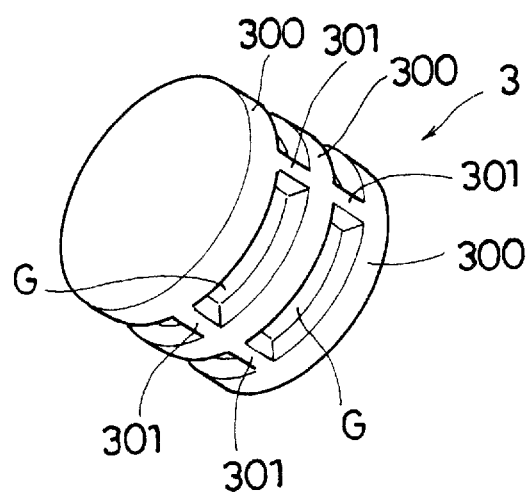
FIG. 11 is a perspective view showing a partition in FIG. 10 on an enlarged scale.

Referring to FIGS. 10 and 11, the partition 3 is provided with a plurality of ring-shaped ribs 300 having grooves (G) therebetween. The adjacent grooves (G) are bridged by other ribs 301 which will be referred to as transverse or bridging ribs. The bridging ribs 301 have the same height as that of the first-mentioned ribs 300. The bridging ribs 301 subdivide the grooves (G) into separate small recesses. The illustrated example has two grooves (G) and four bridging ribs 301 displaced at 90°, thereby obtaining eight equally divided recesses in all. The annular ribs 300 extend at generally a right angle to the axis of the tubular body 1 and the bridging ribs 301.

Figure 12:
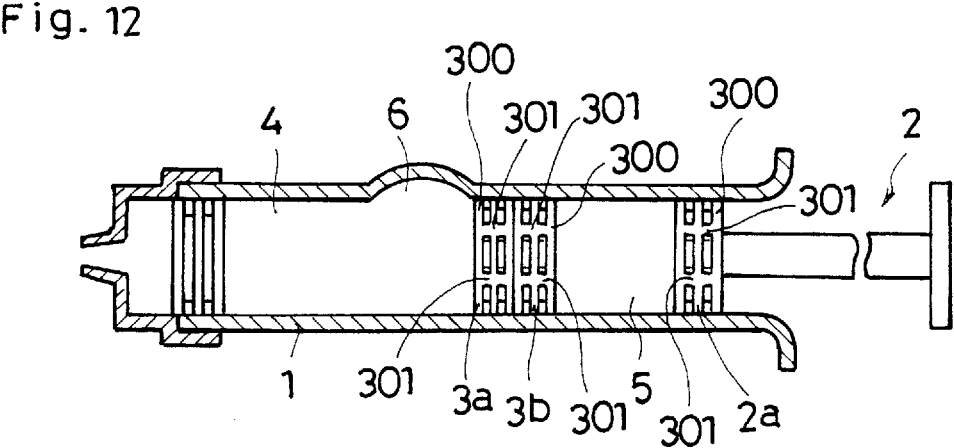
FIG. 12 is a cross-section through a modified version of the example of FIG. 10 in which a partition and a plunger have ring-shaped ribs and bridging ribs.

The subdividing of the grooves (G) by the bridging ribs 301 minimizes the amount of injection liquid remaining in the groove (G), thereby minimizing the amount of injection liquid which remains unused. The greater the number of bridging ribs which are used, the less the amount of injection liquid which remains unused, but as the number of the bridging ribs increases, the friction created between the partition 3 and the inside wall of the tubular body 1 increases, thereby preventing smooth movement of the partition 3 in the tubular body 1. The transverse or bridging ribs act as barriers which prevent the injection liquid from flowing circumferentially about the partition 3. Hence a lesser quantity of injection liquid is trapped in the circumferential grooves (G). As shown in FIG. 12, the partition parts 3a and 3b may also include such transverse or bridging ribs 301. Further, it should be noted that, instead of being flat as shown in FIG. 11, the annular and bridging ribs may typically have a curve or crown to reduce friction created against the inner surface of the tubular body.

EXAMPLE 3

Referring to FIGS. 13(A)–(B) and 14(A)–(E), a further modified version of the invention will be described.

Figure 13A:
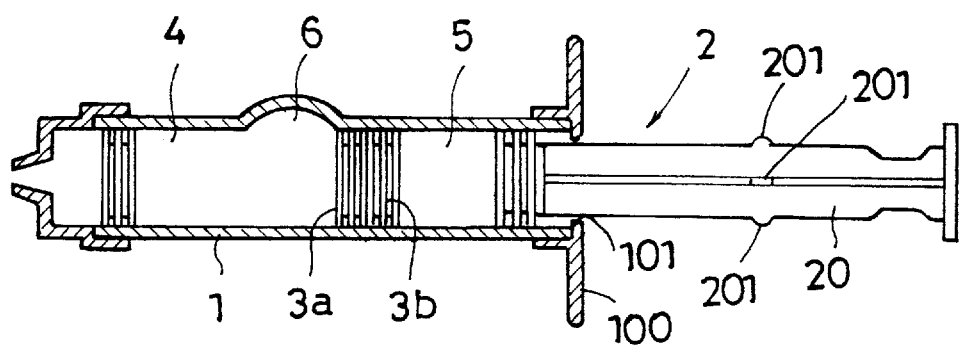
FIGS. 13(A) and 13(B) are cross-sections through a third embodiment of the invention.
Figure 13B:
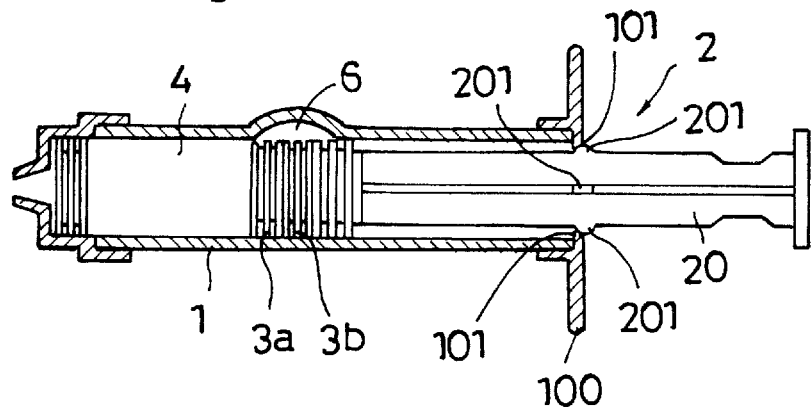

This example is designed to assist a stirring action of the medicinal component P and vehicle L after such are initially mixed in the front compartment so as to obtain a homogeneous injection liquid through a predetermined chemical state, such as dispersing or dissolving, as the case may be. The stirring is facilitated by a swinging of the syringe. In this case, it is difficult to retain the plunger 2 at an appropriate place when the injection liquid is in the front compartment; if the plunger 2 is moved excessively into the tubular body 1, the medicinal component P and vehicle L are likely to be injected through the syringe without reaching a homogeneous state. To solve this difficulty, the tubular body 1 is provided with a disc-shaped fingergrip 100 at the end of the tubular body 1 into which the plunger 2 is inserted. The fingergrip 100 has an inner peripheral rim or syringe portion 101 projecting slightly into the passage for the plunger 2. The plunger 2 has a rod 20 which is provided with projections or nubs 201 on the periphery thereof; in the exemplary embodiment, four projections 201 are displaced at 90° around the axis of the plunger 2. Each of the nubs 201 extends in a radial and axial direction. The nubs 201 are axially spaced from the rim 101 such that the plunger 2 freely slides through the rear compartment 5. The nubs 201 are also axially spaced from the rear end of the push rod so that the plunger 2 slides freely through the front compartment 4. Each projection 201 is located at such a position that it comes into engagement with the inner peripheral rim 101 when the forward end or face of the front part 3a of the partition 3 reaches the outlet or front side (left-hand side) of the bypass 6 as shown in FIG. 13(B) such that the bypass is almost or in fact is shut off relative to the front compartment 4 to minimize or prevent backflow to the bypass 6. At this position, the rear compartment 5 is completely sealed by the plunger 2 to prevent backflow into the push rod region during a shaking of the syringe. It should be noted that the syringe is conservatively constructed so that, even if the push rod 2 is pushed slightly past the nubs 201, the plunger still seals the bypass inlet.

In other words, the length of the plunger 2 is sufficiently long relative to the position of the nubs 201 on the push rod so as to minimize leakage to the rear compartment. The fingergrip 100 is preferably made of resilient synthetic resin to permit the fingergrip 100 to bend or give slightly such that the nubs 201 are disengagable from the fingergrip 100. Alternatively, either the nubs 201, or both the fingergrip 100 and nubs 201, may be resilient.

In operation, as the first step, the plunger 2 is pushed as shown in FIG. 13(B) to the extent that the projections 201 are brought into engagement with the inner peripheral resilient rim 101 and stopped from entering the tubular body 1. During this first step, the vehicle L in the rear compartment 5 is introduced into the front compartment 4 via the bypass 6. While the projections 201 are retained against the inner peripheral resilient rim 101, the syringe is swung to stir the medicinal component P and the vehicle L to obtain a homogeneous mixture. The projections 201 thereby prevent the plunger 2 from being slid further forward such as by centrifugal force created by swinging the syringe. As the second step, after an injection liquid is obtained through a desired action such as dispersing or dissolving of the medicinal component P with the vehicle L, the plunger 2 is pushed by a force which is strong enough to disengage the projections 201 from the inner peripheral resilient rim 101. Then the injection liquid is ejected in a homogeneously mixed state.

Figure 14A:
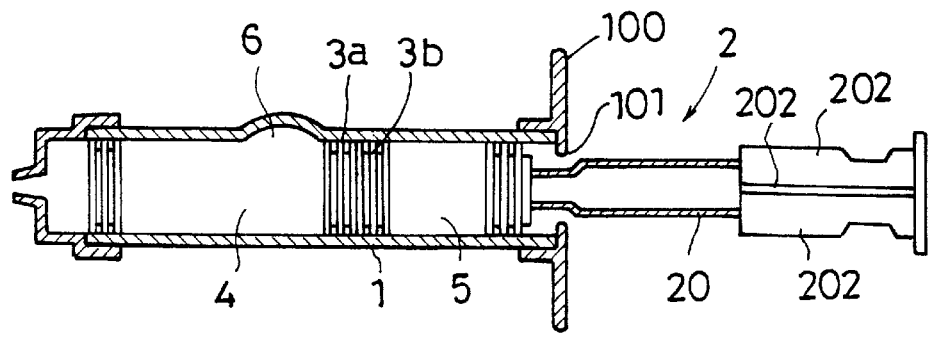
FIGS. 14(A) to 14(E) are views showing a modified version of the third embodiment of FIG. 13.
Figure 14B:
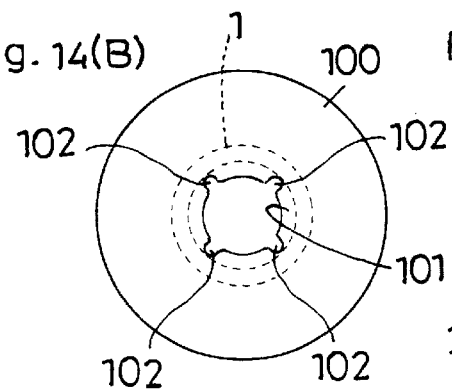
Figure 14C:
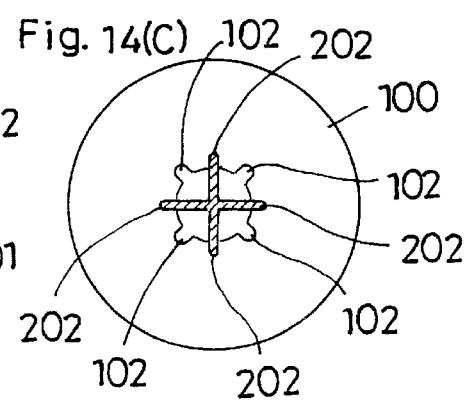
Figure 14D:
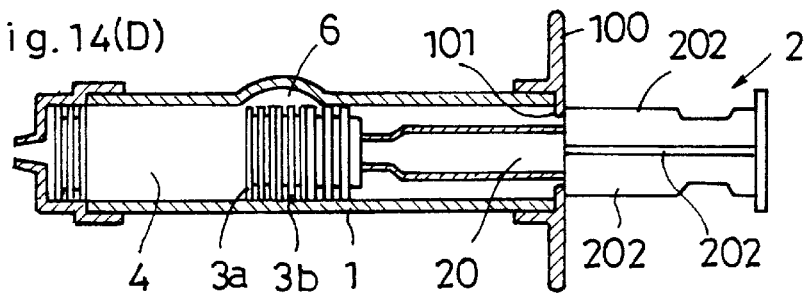
Figure 14E:
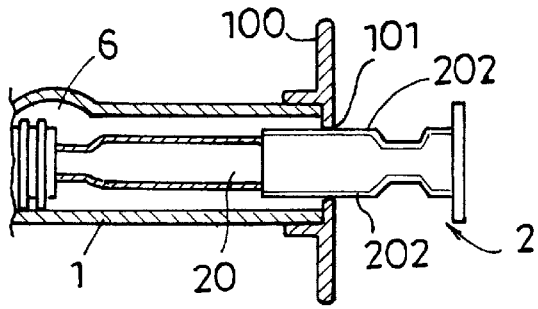
Figure 15:
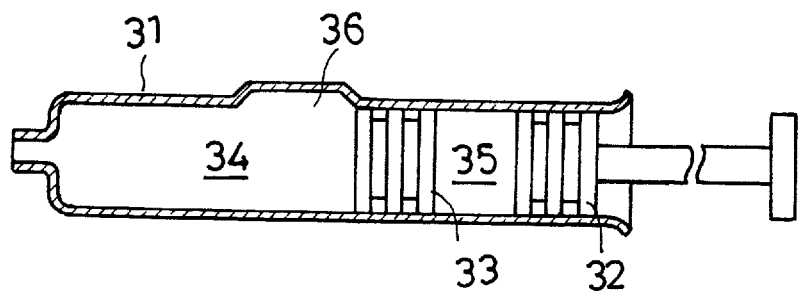
FIGS. 15–18 are cross-sections through a prefilled syringe of a known type, particularly showing the manner of using the syringe.
Figure 16:
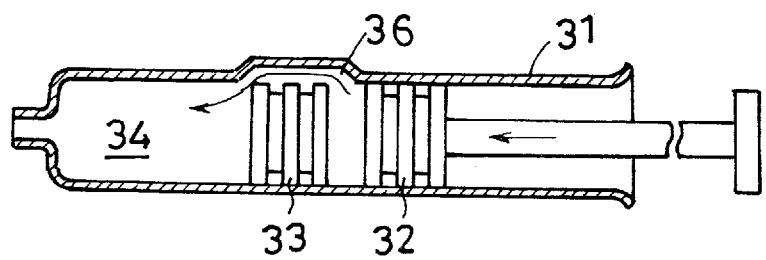
Figure 17:
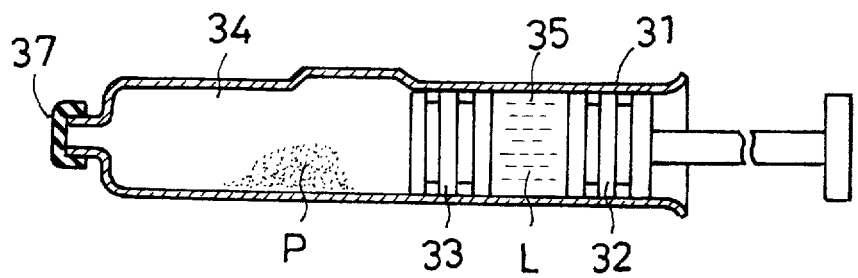
Figure 18:
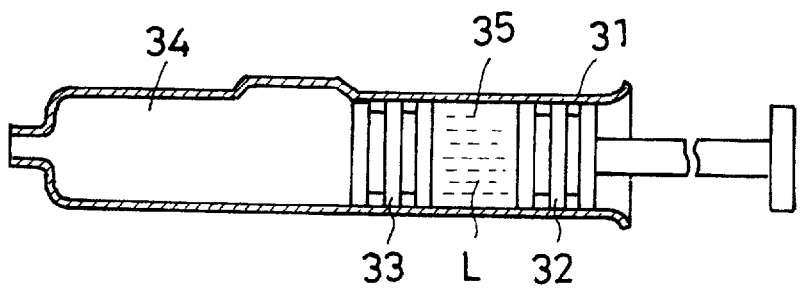
Figure 19:
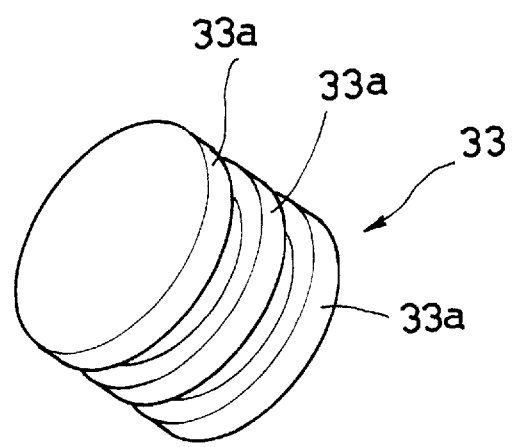
FIG. 19 is a perspective view showing a partition used in the known prefilled syringe shown in FIGS. 15–18.

An alternative example is shown in FIGS. 14(A) to 14(E). This example is characterized by the provision of slots 102 in the inner peripheral rim or syringe portion 101. The illustrated example has four slots 102 displaced at 90°. The rod 20 of the plunger 2 is provided with a number of blades 202 corresponding to that of the slots 102 so that the blades 202 can fit into the slots 102. The blades 202 have a size to permit passage through the respective slots 102 after the push rod 20 has been rotated or turned to match the blades 202 to their respective slots 102. The length from the central axis of the rod 20 up to the top edge of each blade 202 is slightly larger than the inside diameter of the peripheral resilient rim 101 so as to enable each blade 202 to fit in the respective slots 102. The forward end or engagement portion of each blade 202 is axially spaced from the inner peripheral resilient rim 101 before the plunger 2 is actuated. The forward end of each blade 202 is positioned so that each blade 202 can come into engagement with the rear end face of the fingergrip 100 when the forward end of the front part 3*a* of the partition 3 reaches the left-band side of the bypass 6 as shown in FIG. 14(D) such that the front compartment 4 is almost or in is fact is sealed relative to the bypass 6 to prevent backflow into the bypass 6. At this position, the plunger 2 also seals the rear compartment 5 against backflow from the bypass 6.

In using the syringe, the rod 20 is pushed until the front ends of the blades 202 come into engagement with the rear end face of the finger grip 100 as shown in FIG. 14(*c*), which shows the relationship between the blades 202 and the slots 102. The rod 20 is thus prevented from further entering the tubular body 1 when the of the syringe creates a centrifugal force on the plunger 2 and rod 20. At this position, as shown in FIG. 14(D), the front part 3*a* of the partition 3 has reached the left-hand side of the bypass 6 to almost or in fact shut off the bypass 6, and the vehicle L in the rear compartment 5 has completely entered the front compartment 4 as the plunger 2 has engaged the rear stopper. Then the syringe is swung so as to enable the medicinal component P and vehicle L to mix into a homogeneous injection liquid through a predetermined action, such as dispersing or dissolving, as the case may be. Finally the plunger 2 is turned or rotated and again pushed so as to enable the blades 202 to pass through the slots 102 as shown in FIG. 14(E). In this way the injection liquid is ejected through the syringe in a homogeneously mixed state.

What is claimed is:

1. A prefilled syringe for storing at least two substances apart from each other and subsequently mixing the substances in the syringe prior to injection, said prefilled syringe comprising:

a tubular body having front and rear end portions and front and rear compartments, each of said compartments having one of the at least two substances therein, and said rear end portion being sealed by a plunger that is adapted to be axially slid in the tubular body by a push rod;

a bypass stopper plug that is axially slidable in said tubular body and disposed between said front and rear compartments for separating and sealing said front and rear compartments from each other and for sliding by being actuated by sliding of said plunger, said stopper plug having an axial thickness and a front section;

a bypass between said stopper plug and said front end portion of said tubular body for permitting one of the substances in one of said front and rear compartments to bypass said stopper plug so as to be introduced into the other of said front and rear compartments, said bypass having an axial length greater than the axial thickness of said stopper plug, and said stopper plug being slidable to said bypass by sliding of said plunger;

a double-pointed needle having a front end for injection and a rear piercing end, said needle being engagable with said front end portion of said tubular body; and a front plug for sealing said front end portion of said tubular body, said front plug having a front central recess for guiding said rear piercing end of said needle into said front plug;

wherein said stopper plug has a front central recess axially aligned with said front central recess of said front plug for housing said rear piercing end of said needle after said needle has pierced said front plug.

2. A prefilled syringe for storing at least two substances apart from each other and subsequently mixing the substances in the syringe prior to injection, said prefilled syringe comprising:

a tubular body having front and rear end portions and front and rear compartments, each of said compartments having one of the at least two substances therein, and said rear end portion being sealed by a plunger that is adapted to be axially slid in the tubular body by a push rod;

a bypass stopper plug that is axially slidable in said tubular body and disposed between said front and rear compartments for separating and sealing said front and rear compartments from each other and for sliding by being actuated by sliding of said plunger, said stopper plug having an axial thickness and a front end;

a bypass between said stopper plug and said front end portion of said tubular body for permitting one of the substances in one of said front and rear compartments to bypass said stopper plug so as to be introduced into the other of said front and rear compartments, said bypass having an axial length greater than the axial thickness of said stopper plug, and said stopper plug being slidable to said bypass by sliding of said plunger;

a double-pointed needle having a front end for injection and a rear piercing end, said needle being engagable with said front end portion of said tubular body;

a front plug for sealing said front end portion of said tubular body, said front plug having a front central recess for guiding said rear piercing end of said needle into said front plug and a rear end; and another central recess in one of said stopper plug and said front plug that is axially aligned with said front central recess of said front plug for housing said rear piercing end of said needle after said needle has pierced said front plug;

wherein said front end of said stopper plug is convex and said rear end of said front plug is concave, said stopper plug and said front plug engaging each other after the substances have been injected.

3. The prefilled syringe of claim 2, wherein the other said central recess is disposed in said front end of said stopper plug.

4. The prefilled syringe of claim 2, wherein the other said central recess is disposed in said rear end of said front plug.

5. A prefilled syringe for storing at least two substances apart from each other and subsequently mixing the substances in the syringe prior to injection, said prefilled syringe comprising:

a tubular body having front and rear end portions and front and rear compartments, each of said compartments having one of the at least two substances therein, and said rear end portion being sealed by a plunger that is adapted to be axially slid in the tubular body by a push rod;

a bypass stopper that is axially slidable in said tubular body and disposed between said front and rear compartments for separating and sealing said front and rear compartments from each other and for sliding by being actuated by sliding of said plunger, said bypass stopper comprising a first stopper plug and a second stopper plug, said first stopper plug being located in front of said second stopper plug, and said bypass stopper having an axial thickness;

a bypass between said bypass stopper and said front end portion of said tubular body for permitting one of the substances in one of said front and rear compartments to bypass said bypass stopper so as to be introduced into the other of said front and rear compartments, said bypass having an axial length greater than the axial thickness of said bypass stopper, and said bypass stopper being slidable to said bypass by sliding of said plunger;

a double-pointed needle having a front end for injection and a rear piercing end, said needle being engagable with said front end portion of said tubular body; and a front plug for sealing said front end portion of said tubular body, said front plug having a front central recess for guiding said rear piercing end of said needle into said front plug and a rear end; and another central recess in one of said first stopper plug and said front plug that is axially aligned with said front central recess of said front plug for housing said rear piercing end of said needle after said needle has pierced said front plug.

6. The prefilled syringe of claim 5, wherein the other said central recess is disposed in said rear end of said front plug.

* * * * *

UNITED STATES PATENT AND TRADEMARK OFFICE
CERTIFICATE OF CORRECTION

PATENT NO. : 5,865,799
DATED : February 2, 1999
INVENTOR(S) : Nobuo TANAKA ET AL.

It is certified that error appears in the above-identified patent and that said Letters Patent is hereby corrected as shown below:

ON THE TITLE PAGE:

Item [62], line 1, change "530,674" to --530,764--;
line 2, change "52,622" to --52,682--.

Signed and Sealed this

Seventh Day of September, 1999

Q. TODD DICKINSON

Attest:

Attesting Officer    Acting Commissioner of Patents and Trademarks

UNITED STATES PATENT AND TRADEMARK OFFICE
CERTIFICATE OF CORRECTION

PATENT NO. : 5,865,799
DATED : February 2, 1999
INVENTOR(S) : Nobuo Tanaka, et. al.

It is certified that error appears in the above-indentified patent and that said Letters Patent is hereby corrected as shown below:

Title page, item [73], Assignee: after "Industries" insert --, Ltd.--

Signed and Sealed this

Nineteenth Day of October, 1999

Attest:

Q. TODD DICKINSON

*Attesting Officer*    *Acting Commissioner of Patents and Trademarks*